(12) United States Patent
Latt et al.

(10) Patent No.: US 12,702,462 B2
(45) Date of Patent: Aug. 11, 2026

(54) CANNULATED BONE SCREW EXTRACTION DEVICE AND METHODS OF USE THEREOF

(71) Applicant: Arizona Board of Regents on Behalf of the University of Arizona, Tucson, AZ (US)

(72) Inventors: L. Daniel Latt, Tucson, AZ (US); Carlos Urrea-De La Puerta, Tucson, AZ (US); Carolina Gomez Llanos, Tucson, AZ (US); Emilio Araiza, Tucson, AZ (US); Erick De Leon, Tucson, AZ (US); Eva Richter, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 440 days.

(21) Appl. No.: 18/310,522

(22) Filed: May 1, 2023

(65) Prior Publication Data

US 2023/0346445 A1 Nov. 2, 2023

Related U.S. Application Data

(60) Provisional application No. 63/337,159, filed on May 1, 2022.

(51) Int. Cl.
*A61B 17/92* (2006.01)
*A61B 17/86* (2006.01)

(52) U.S. Cl.
CPC ............ *A61B 17/92* (2013.01); *A61B 17/864* (2013.01)

(58) Field of Classification Search
CPC ... A61B 17/8875; A61B 17/92; A61B 17/864; A61B 2017/0411; B25B 27/18
See application file for complete search history.

(56) References Cited

U.S. PATENT DOCUMENTS

| | | | | | |
|---|---|---|---|---|---|
| 1,604,032 | A | * | 10/1926 | Ferrell | B25B 27/18 81/53.2 |
| 1,798,944 | A | * | 3/1931 | Jackman | B25B 27/18 81/53.2 |
| 2,013,923 | A | * | 9/1935 | Naccarato | B25B 27/18 81/53.2 |
| 2,243,717 | A | * | 5/1941 | Godoy | A61B 17/742 411/548 |
| 2,678,217 | A | * | 5/1954 | King | B25B 27/18 279/2.15 |
| 2,941,429 | A | * | 6/1960 | Mason | B21D 1/065 81/463 |
| 4,084,457 | A | * | 4/1978 | Berg | B25C 11/02 81/424.5 |

(Continued)

*Primary Examiner* — David W Bates
(74) *Attorney, Agent, or Firm* — BLANK ROME LLP

(57) ABSTRACT

A surgical instrument for the removal of cannulated screws or members, the device includes an elongated body comprising a first end, a second end opposite the first end, and a screw tip contact member disposed proximate the second end. The elongated body is formed of a resilient material. The elongated body has a first longitudinal axis and the elongated body further has a portion proximate the screw tip contact member that is canted relative to the longitudinal axis. Methods of using the device to remove a cannulated bone screw from bone are also provided.

13 Claims, 6 Drawing Sheets

(56) References Cited

U.S. PATENT DOCUMENTS 4,204,308 A * 5/1980 Marling .................. B25C 11/02 81/53.2
4,335,632 A * 6/1982 Irwin ...................... B25B 13/54 81/449
4,939,959 A * 7/1990 Rokita .................. B25B 23/101 81/13
5,078,718 A * 1/1992 Moll .................. A61B 17/8847 606/86 R
5,190,551 A * 3/1993 Chin .................. A61B 17/8847 606/86 R
5,299,105 A * 3/1994 Arntzen .................. B25B 27/18 81/53.2
5,484,440 A * 1/1996 Allard ................ A61B 17/8886 411/407
5,749,878 A * 5/1998 Bracy ................ A61B 17/0469 606/232
5,766,180 A * 6/1998 Winquist ............. A61B 17/921 606/62
5,904,690 A * 5/1999 Middleman .... A61B 17/320016 606/113
6,004,321 A * 12/1999 Graser ................... A61B 17/92 606/53
6,746,451 B2 * 6/2004 Middleton ......... A61B 17/1664 606/180
7,179,024 B2 * 2/2007 Greenhalgh ............ B23B 51/02 606/80
7,264,622 B2 * 9/2007 Michelson ......... A61B 17/1671 606/86 A
7,329,228 B2 * 2/2008 Burbank ................ A61B 10/04 600/564
7,766,917 B2 * 8/2010 Kugler ................... A61B 17/92 606/86 R
8,221,425 B2 * 7/2012 Arcenio ............. A61B 17/1671 606/84
8,454,621 B2 * 6/2013 DeRidder ............. A61F 2/4611 623/17.16
8,535,357 B2 * 9/2013 Stone ................... A61B 17/866 606/300
8,728,088 B2 * 5/2014 LeBeau .................. A61B 17/88 606/86 R
8,808,307 B2 * 8/2014 Robinson ........... A61B 17/7032 606/104
9,028,499 B2 * 5/2015 Keyak .................. A61N 5/1014 606/79
9,662,123 B2 * 5/2017 Tally .............. A61B 17/320708
10,820,936 B2 * 11/2020 Ortiz .................. A61B 17/7082
10,966,842 B2 * 4/2021 Kulper .................. A61F 2/4603
2004/0154438 A1 * 8/2004 Kozak ..................... B25B 27/18 81/53.2
2005/0149051 A1 * 7/2005 Hansson ................ A61B 17/92 606/104
2007/0051215 A1 * 3/2007 Petillo ................... B25B 23/106 81/436
2007/0079674 A1 * 4/2007 Rupp .................... B25B 23/108 81/53.2
2007/0260250 A1 * 11/2007 Wisnewski .......... A61B 17/864 606/86 A
2007/0270880 A1 * 11/2007 Lindemann ........ A61B 17/8891 606/104
2008/0065072 A1 * 3/2008 Spitler ............... A61B 17/7083 606/270
2008/0190252 A1 * 8/2008 Parrott .................. B25B 23/108 81/451
2008/0255555 A1 * 10/2008 Justis ..................... A61B 17/17 606/60
2008/0269768 A1 * 10/2008 Schwager ............. B25B 23/108 81/436
2011/0046682 A1 * 2/2011 Stephan ................. A61B 17/84 606/305
2011/0184420 A1 * 7/2011 Barnhouse ....... A61B 17/32002 606/84
2012/0004664 A1 * 1/2012 Paul ........................ A61F 2/461 606/100
2012/0239052 A1 * 9/2012 Beger ................ A61B 17/8897 606/301
2013/0006278 A1 * 1/2013 Mayer ................ A61B 17/8645 606/151
2013/0090698 A1 * 4/2013 Nuckley ............ A61B 17/8888 606/104
2013/0096565 A1 * 4/2013 Fritzinger .............. A61B 90/06 606/102
2014/0366482 A1 * 12/2014 Dougherty ............ F16B 37/127 52/745.15
2015/0133944 A1 * 5/2015 Kortenbach ........... A61B 90/06 216/48
2015/0283626 A1 * 10/2015 Thomas .................. B25B 27/18 81/53.2
2015/0289915 A1 * 10/2015 Hansson ............ A61B 17/8685 606/328
2015/0320464 A1 * 11/2015 Schmidt ............... A61B 17/864 606/304
2016/0354074 A1 * 12/2016 Miller ................ A61B 17/8605
2017/0303981 A1 * 10/2017 Myers ................ A61B 17/8888
2017/0312001 A1 * 11/2017 Naglapura ......... A61B 17/8888
2018/0221042 A1 * 8/2018 Hamsch ................. A61B 17/24
2018/0235684 A1 * 8/2018 Hawkes ................ B25B 23/108
2020/0093522 A1 * 3/2020 Zink .................. A61B 17/7091
2020/0289183 A1 * 9/2020 Krause ................ F16B 25/0005
2021/0393394 A1 * 12/2021 Zink .................. A61B 17/0401
2025/0082381 A1 * 3/2025 Savage .............. A61B 17/8635

* cited by examiner

28

24
24'
29
27
26

CANNULATED BONE SCREW EXTRACTION DEVICE AND METHODS OF USE THEREOF

CROSS REFERENCE TO RELATED APPLICATIONS

This application claims the benefit of the filing date of U.S. Provisional Application No. 63/337,159, filed on May 1, 2022, entitled "CANNULATED BONE SCREW EXTRACTION DEVICE AND METHODS OF USE THEREOF." The entirety of the foregoing is hereby incorporated by reference.

FIELD OF THE INVENTION

The field of this invention generally relates to an improved method and apparatus for the nondestructive removal of cannulated surgical screws from mammalian subjects.

BACKGROUND OF THE INVENTION

In 2017, approximately 22.3 million orthopedic surgeries were performed throughout the world. Certain common orthopedic surgeries (e.g., hip repair surgery, spinal vertebral fusion surgery) involve the use of cannulated screws to stabilize bones and/or bone fragments during the healing process, and to provide a pathway to administer medicine. Post-operative complications, such as hardware failure and infection can occur at the surgical site. Follow-up surgery is often needed to remove loose hardware (e.g., cannulated) and infected tissue.

Devices, kits and methods of using same devices and kits are available to extract screws from bones at surgical sites. However, operators continue to encounter problems when attempting to extract screws from biological tissue (e.g., bone). Accordingly, there is still a need for improved devices and methods for extracting surgical screws.

DESCRIPTION

Definitions

Figure 1:
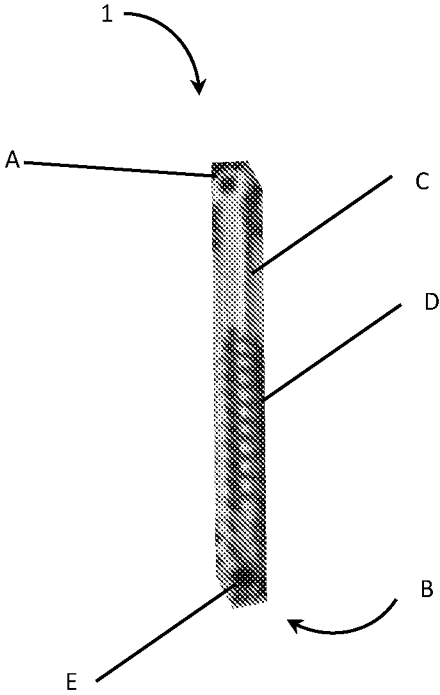
FIG. 1 is a perspective view of a cannulated bone screw.

For the purposes of promoting an understanding of the principles of the invention, reference will now be made to certain embodiments and specific language will be used to describe the same. It will nevertheless be understood that no limitation of the scope of the invention is thereby intended, and alterations and modifications in the illustrated invention, and further applications of the principles of the invention as illustrated therein are herein contemplated as would normally occur to one skilled in the art to which the invention relates.

Unless defined otherwise, all technical and scientific terms used herein have the same meaning as commonly understood by one of ordinary skill in the art to which this invention pertains.

For the purpose of interpreting this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used).

The use of "or" means "and/or" unless stated otherwise.

The use of "a" or "an" herein means "one or more" unless stated otherwise or where the use of "one or more" is clearly inappropriate.

The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, the term "about" refers to a ±10% variation from the nominal value. It is to be understood that such a variation is always included in any given value provided herein, whether or not it is specifically referred to.

As used herein, the term "biocompatible surface" refers to a surface of an object, the surface having the ability to be in contact with a patient without producing a substantial adverse effect on a tissue or biological system of the patient.

As used herein, the term "patient" refers to a mammalian organism (e.g., a human, a wild or domestic animal) being treated for a medical condition (e.g., a broken bone).

As used herein, the term "handle" refers to a part of an object that may be held, seized, or grasped.

As used herein, the term "bone screw cannula" refers to a hollow space extending through a bone screw (e.g., from the "head" end of the screw to the "tip" end of the screw). The cannula permits an operator (e.g., a surgeon) to place a guidewire extending through the bone screw cannula and into a surgical area wherein the screw is moved along the guidewire to an end of the wire that indicates the proper point where the wire is withdrawn from the screw and the screw is threadably inserted into a bone.

As used herein, the term "cannulated" refers to an object that is defined by a cannula in its interior.

As used herein, the term "elastic material" refers to an object that is defined with a high elastic modulus and whose deformation is characterized by elastic deformation As used herein, the term "resilient" refers to a property of a substance or object which confers the ability of the substance or object to recoil or spring back into shape after bending, stretching, or being compressed.

As used herein, the term "handle" refers to a part of an object that may be held, seized, or grasped.

As used herein, the term "manual force" refers to the effort exerted by the user of the apparatus to impart a force by way of mechanical advantage onto a fastener.

As used herein, a "chuck" refers to a clamp-like attachment that holds a wire or an elongated wire-like structure. An end of the wire or wire-like structure fits into and is secured by the chuck.

The present disclosure generally relates to improved methods and devices for the nondestructive removal of surgical screws from mammalian subjects. "Nondestructive removal", as used herein, refers to the removal of a surgical screw without substantially degrading (e.g., fragmenting) the surgical screw. The methods and apparatuses are particularly suitable for the removal of cannulated surgical screws. In addition, the assemblies and methods of the present disclosure are particularly useful for the removal of screws that are disposed in a bone but are no longer threadably engaged (e.g., have "lost their purchase") with the bone. "Threadably engaged", as used herein, refers to screws that are surrounded by tissue (e.g., bone tissue) that has enough integrity such that turning the threaded screw clockwise or counterclockwise relative to its longitudinal axis will result in movement of the screw along its longitudinal axis.

Advantageously, the assemblies of the present disclosure include features that permit the operator to firmly grasp the body of a cannulated screw at a point that is distal to the screw head, thus providing the ability for the operator to engage the opposite (head) end of the screw with other features (e.g., the proximal screws engagement element described hereinbelow, a bone screw screwdriver) of the assemblies. Further, as a result of the assembly of the present disclosure gripping the cannulated screw at two points and forcing the screw from the bottommost (i.e., tip) portion into the tool, the assembly is able to grab and stabilize the screw significantly more effectively than previous assemblies.

FIG. 1 shows one embodiment of a cannulated bone screw 1. The screw 1 comprises an elongated body with a head A at one end and a tip B at the opposite end and a shank C disposed therebetween. Typically, a thread D is disposed between the head A and the tip B. In the illustrated embodiment of FIG. 1, the thread D is disposed proximate the tip B. A cannula E extends through the body of the screw 1 from the head A and the tip B and forms a hollow channel that passes through the screw from the head to the tip.

Figure 2:
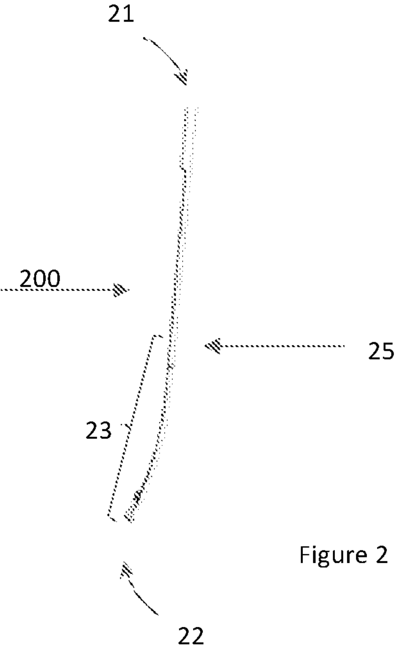
FIG. 2 is a perspective view the screw tip engagement device according to the present disclosure.

In one aspect, the present disclosure provides a screw tip engagement device for extracting a bone screw from biological tissue (e.g., a bone). FIG. 2 shows one embodiment of the screw tip engagement device 200 according to the present disclosure. The screw tip engagement device 200 comprises a first end 21, a second end 22, and a deformably resilient screw tip contact member 23 disposed proximate the second end. The screw tip engagement device 200 can be fabricated from a resilient material selected from the group consisting of spring steel with a low-alloy manganese, medium-carbon steel or high-carbon steel with a high yield strength, or a combination thereof. It is further envisioned that the screw tip engagement device 200 may be constructed of a memory metal such as nitinol. Such materials may assume an alternative shape upon heating. In addition, the screw tip engagement device 200 is configured to hold a tension force sufficient to engage and remove the screw from a bone without breaking or disintegrating while the tension force is held. The screw tip contact member 24 defines gripping region (e.g., the hook-like bend 26 and/or the point 27) that is configured to engage the bottom of a cannulated screw outside of the screw cannula.

The screw tip contact member retains elastomeric properties when compressed, thereby allowing it to resume an original shape when decompressed. In the illustrated embodiment of FIG. 2, the screw tip engagement device 200 comprises a deformably resilient wire.

Figures 3A, 3B:
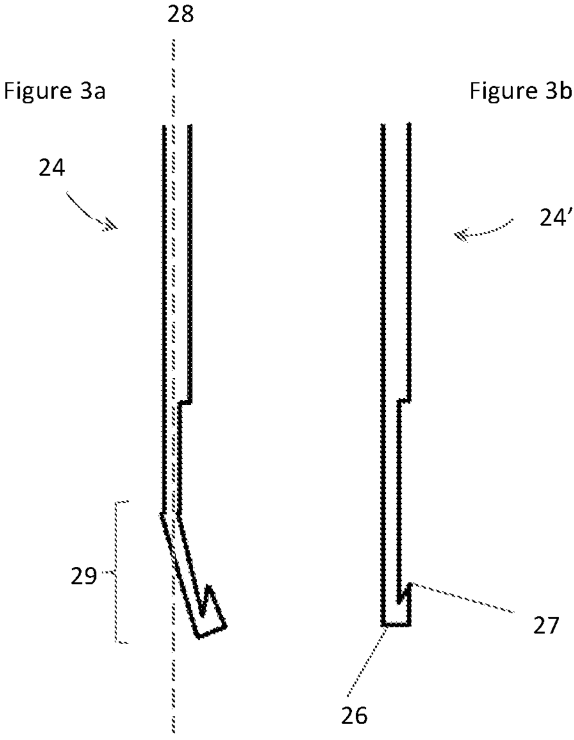
FIGS. 3*a* and 3*b* are schematic side views of a screw tip contact element of the device of FIG. 1 in a native configuration and in a deformed configuration, respectively.

FIG. 3*a* shows the screw tip engagement device 200 in a native (e.g., "relaxed" or "nontensioned"), configuration that is capable of interaction (e.g., engagement) with a bottom portion of a cannulated screw. When in the native configuration, the screw tip engagement device 200 has a longitudinal axis 28 and a canted portion 29 proximate the screw tip contact member 24. FIG. 3*b* shows a screw tip contact member 24' in a deformed configuration, as may occur when the resilient member is passed through a cannel (e.g., cannula of a bone screw) that is not a sufficient diameter to permit the screw tip contact member 24' to retain the bend 26 of the screw tip contact member as it passes therethrough.

In use, the second end 22 of the screw tip engagement device 200 is passed into and through the cannula of a cannulated bone screw until at least a portion of the screw tip contact member 24 emerges from outside the tip end of the screw. Subsequently, a force (e.g., manual force) is applied to the screw tip engagement device 200 in a direction that is substantially aligned with the longitudinal axis of the bone screw and away from the point of entry of the screw into the bone and thereby facilitating movement of the screw out of the bone. Applying the force can comprise gripping the screw tip engagement device 200 proximate the first end using a gripping tool (e.g., pliers, a clamp, a chuck, and the like). In those implementations, the force can be applied directly to the gripping tool and, thus, indirectly to the screw tip engagement device.

In another aspect, the present disclosure provides an assembly for extracting a cannulated bone screw that is partially or completely disposed in a tissue (e.g., bone). FIG. 3 show a perspective view of one embodiment of an assembly 100 according to the present disclosure. The assembly comprises a proximal screw engagement element 11, shown in more detail in FIG. 4, having a third end 12, a fourth end 13 opposite the third end, and a first hollow channel (not shown) extending from a first opening (not shown) at the third end 12 to a second opening (not shown) at the fourth end 13. The fourth end 13 is configured to firmly engage a portion of a cannulated bone screw proximate the screw head. In some embodiments, the fourth end comprises a cavity (not shown) dimensioned to receive the head region of a bone screw or a protrusion (e.g., similar to the drive of a Phillips head screwdriver) that is capable of engaging a cavity in the head of the bone screw.

Figure 4:
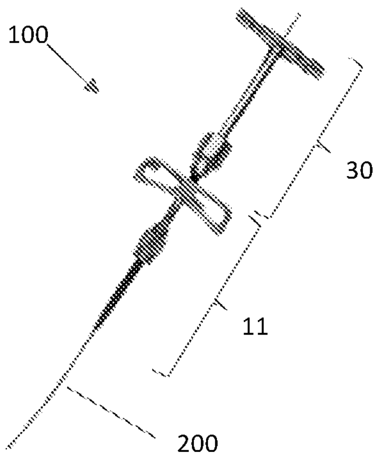
FIG. 4 is a perspective view of one embodiment of an assembly according to the present disclosure.

The assembly further comprises any embodiment of the screw tip engagement device 200 described herein. In the assembly 100, the screw tip engagement device 200 is disposed in the first hollow channel 14 such that the first end 21 extends outside the first hollow channel at the third end 12 of the proximal screw engagement element 11 and the second end of the screw tip engagement device, including the screw tip contact member 23, extends outside the first hollow channel at the fourth end of the proximal screw engagement element, as shown in FIG. 4.

In some embodiments, the proximal screw engagement element 11 of the assembly 100 further includes a first handle 15 that, through manual force, may be rotated about the screw tip engagement device 200 disposed therein. Upon such rotation, it is envisioned that a screw in contact with the proximal screw engagement element 100 would rotate in unison with the proximal screw engagement element and, optionally, the screw tip engagement device.

In some embodiments, the screw tip engagement device 200 optionally includes a handle (not shown) proximate the first end 21, such that through manual force applied to the handle, tension may be imparted onto a screw tip engagement device operatively engaged with the tip of a cannulated bone screw.

In some embodiments, the screw tip engagement device is disposed within the hollow channel of the proximal screw engagement element wherein the hollow channel defines a travel path (e.g., to a cannulated screw, travel path not shown) for the screw tip engagement device. The relatively rigid elements of the travel path (e.g., the proximal screw engagement member, the cannulated screw) of the travel path deform the screw tip contact member as it passes therethrough due to the elastomeric properties of the screw tip contact member. In some embodiments, the fourth end of the proximal screw engagement element 11 comprises a screwdriver assembly (not shown) that is adapted to operatively engage the screwhead of a conventional cannulated bone screw.

In any embodiment, components of the assembly 100 can be fabricated (e.g., by 3-D printing) using a biocompatible material. Nonlimiting examples of biocompatible materials include 304 stainless steel, 316 stainless steel, SAE 316 stainless steel, titanium or titanium alloys, Inconel, low carbon steel, alloys of steel including chromium, nickel, molybdenum, aluminum, austenitic stainless steel, and a combination of any two or more of the foregoing materials. Alternatively, or additionally, the material used to fabricate the assembly, or tissue-contacting components thereof. can be coated (e.g., during or after fabrication) with a biocompatible coating material.

In any embodiment of the assembly of the present disclosure, the tip contact member 24 is adapted to translate through the interior opening of a cannulated screw. While so translating within a cannulated screw, it is envisioned that the screw tip contact member 24 will assume a secondary position (e.g., as shown in FIG. 3*b*) having a more linear shape whose profile does not restrict movement therethrough. It is further contemplated that the screw tip contact member 24 element is able to transition from the interior surface of the hollow channel 14 to the cannulated screw surface. As depicted in FIG. 3*b*, the screw tip contact member 24 includes a bend 26 and a point 27, wherein the bend and the point are adapted to engage about the bottommost surface (e.g., the tip) of a cannulated screw and firmly grasp the screw, and while so grasped, apply an upward force to the cannulated screw. This upward force may reengage threads that have lost purchase in a bone. Upon reengagement of threads, the screw may be rotated by the first handle 15 and removed in conventional fashion. Advantageously, because this feature gives the assembly 100 two points of engagement with a cannulated screw, cannulated screws can be more efficiently and reliably removed using an assembly of the present disclosure.

Figure 5:
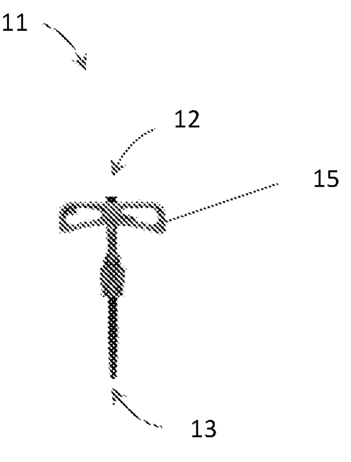
FIG. 5 is a perspective schematic view of the proximal screw engagement element of the assembly of FIG. 1.
Figure 6:
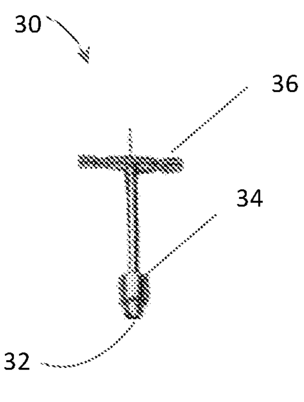
FIG. 6 is a perspective view of the gripping element of the assembly of FIG. 4.

Optionally, an assembly 100 of the present disclosure further comprises a gripping element 30 (see FIGS. 4 and 5) configured to grip the screw tip engagement device 200. In some embodiments, the gripping element may resemble a pliers, a clamp, or a gripping element, for example. The gripping element of the illustrated embodiment of FIGS. 4 and 5 resembles a gripping element. The gripping element comprises hollow body 32 into which the first end 21 of the screw tip engagement device 200 can be inserted and held by the gripping element 34. In some embodiments, the gripping element 34 operates in a manner analogous to a drill bit chuck in an electric drill or a manual drill). In some embodiments, the screw tip engagement device 200 can pass completely through the hollow body of the gripping element 30 Optionally, the gripping element 30 comprises a second handle 36.

In another embodiment, a kit is envisioned which includes: any embodiment of a proximal screw engagement element as described herein and, any embodiment of a screw tip engagement device as described herein.

It is contemplated that the proximal screw engagement element 11 may comprise a first handle 15 that can be manually manipulated. The handle can be used to rotate the assembly or parts thereof.

In certain embodiments, it is envisioned that the screw tip engagement device is a deformably resilient wire comprising a hook structure 23 proximate the second end 22. In some embodiments, the wire is constructed out of a material characterized by elastic properties that may assume an alternative shape under stress. The hook structure 23 can elastically bias toward the wire when the second end of the wire is passed through the travel path of a hollow channel that is not deformed by the screw tip contact member passing through it. The screw tip contact member 23 is further defined as having a native (non-compressed) state of a hook and a bend.

Components of the assemblies of the present disclosure can be produced using processes and materials known in the art. The material used to make the components may influence the process selected to manufacture the component. Non-limiting examples of suitable manufacturing processes include metal stamping, molding, and 3-D printing.

In use, assemblies of the present disclosure can be used to remove cannulated screws from bones even if the screw has lost purchase in the bone or become stripped. The hook element which is extended through the cannula tube of the screw is adapted to engage with the bottom of the screw, and while so engaged, exert an upward force thereupon, forcibly reengagement element the screw threads with the surrounding material. Further, this upward force encourages connection with the proximal screw engagement element member more firmly securing the screw to the proximal screw engagement element. Critically, by providing two points of contact, the screw may be more effectively and reliably removed during operation.

In another aspect, the present disclosure provides a method for extracting a cannulated screw from a bone, the method comprising extracting the cannulated screw from the bone using the screw tip engagement device or the assembly of any one of the embodiments described herein.

In one implementation, the method comprises passing the second end of any embodiment of the screw tip engagement device disclosed herein through a cannula of a cannulated screw that is disposed in the bone, where in the cannulated screw has a screw head, a screw tip, and a screw longitudinal axis that extends from the screw head to the screw tip; after the screw tip contact member of the screw tip engagement device has passed through the cannula of the cannulated screw and the canted portion is disposed in the native state, applying a force (e.g., a manual force) to the screw tip engagement device proximate first end of the screw tip engagement device, wherein the force is applied in a direction generally along the screw longitudinal axis and away from the screw head; and withdrawing the cannulated screw from the biological tissue.

In these embodiments, the method is useful for retrieving cannulated bone screws from bones in which the screws have "lost their purchase" and can no longer be removed using conventional screwdriver techniques. Surprisingly, in some embodiments, the screw tip engagement device may be the only device needed to extract the bone screw. In any of the above embodiments, the method further can comprise while maintaining the applied force, using an accessory tool (e.g., a screwdriver) to extract the screw from the bone. In any of the above embodiments, the method further can comprise using a guide wire to locate the cannulated screw and/or to guide the screw tip engagement device to the cannulated screw.

In any of the above embodiments, the method further comprises using the assembly of any one of the embodiments described herein to extract the screw. In these embodiments, the method comprises passing the second end of the screw tip engagement device through a cannula of a cannulated screw that is disposed in the biological tissue, wherein the cannulated screw has a screw head, a screw tip, and a screw longitudinal axis that extends from the screw head to the screw tip; after the hook of the screw tip engagement device has passed through the cannula of the cannulated screw and thereby reformed the hook, applying a force to the screw tip engagement device proximate the first end, wherein the force is applied in a direction along the screw longitudinal axis and away from the screw head; and withdrawing the cannulated screw from the biological tissue. In any of these embodiments, the method further comprises, prior to the applying the force to screw, engagement element a portion of the screw with the second end of the proximal screw engagement element. In any of these embodiments, the portion of the screw comprises the screw head.

LIST OF EMBODIMENTS

The following examples and examples are provided solely to illustrate the present invention and are not intended to limit the scope of the invention, described herein.

Embodiment 1

An assembly, comprising: a proximal screw engagement element having a third end, a fourth end opposite the third end, and a first hollow channel extending from the third end to the fourth end; wherein the fourth end is configured to engage a portion of a cannulated bone screw; a screw tip engagement device comprising a first end, a second end and a screw tip contact member disposed proximate the second end; wherein the screw tip engagement device is disposed in the first hollow channel such that the first end of the screw tip engagement device extends outside the third end of the first hollow channel and the second end of the screw tip engagement device extends outside the fourth end of the first hollow channel; and optionally, a gripping element holding the screw tip engagement device proximate the first end of the screw tip engagement device.

The assembly of embodiment 1, wherein the proximal screw engagement element further comprises a first handle.

The assembly of embodiment 1 or embodiment 2, wherein the gripping element further comprises a second handle.

The assembly of any one of embodiments 1 through 3, wherein the gripping element further comprises a second hollow channel extending therethrough, wherein a portion of the screw tip engagement device proximate the first end extends into the second hollow channel.

The assembly of embodiment 4, wherein the portion of the screw tip engagement device proximate the first end extends through the second hollow channel.

The assembly of any one of embodiments 1 through 5, wherein the fourth end comprises a screwdriver assembly.

The assembly of any one of embodiments 1 through 6, wherein the screw tip engagement device and the proximal screw engagement element have exterior surfaces that are composed of biologically compatible material.

The assembly of embodiment 7, wherein the screw tip engagement device comprises a deformably resilient wire.

The apparatus of embodiment 8, wherein the wire is composed of an elastic material selected from the group consisting of spring steel with a low-alloy manganese, medium-carbon steel or high-carbon steel with a high yield strength, or a combination thereof.

The apparatus of any one of embodiments 1 through 9, wherein the proximal screw engagement element is rotatable about the wire independent of the gripping element.

The apparatus of any one of embodiments 1 through 10, wherein the screw tip engagement device is adapted to pass through a cannula of a cannulated screw.

The apparatus of any one of embodiments 1 through 11, wherein said screw tip contact member comprises a bend and a point.

Embodiment 2

A kit, comprising: a proximal screw engagement element having a third end, a fourth end opposite the third end, and a hollow channel extending from the third end to the fourth end; wherein the fourth end is configured to hold a portion of a cannulated bone screw; a screw tip engagement device comprising a first end, a second end and a screw tip contact member disposed proximate the second end; and a screw tip engagement device grasping element configured to hold the screw tip engagement device in a position relative to the proximal screw engagement element.

The kit of embodiment 2, wherein the proximal screw engagement element further comprises a first handle.

The kit of embodiment 13 or 14, wherein the screw tip engagement device grasping element further comprises a second handle.

The kit of any one of embodiment 13 through 15, wherein the screw tip engagement device grasping element further comprises a second hollow channel extending therethrough.

The kit of any one of embodiment 13 through 16, wherein the screw tip engagement device comprises a deformably resilient wire comprising a hook structure proximate the second end.

The kit of embodiment 17, wherein the hook structure can elastically bias toward the wire when the second end of the wire is passed through a hollow channel that is not deformed by the screw tip contact member passing through it

Embodiment 3

A method for removing a cannulated screw from biological tissue, the method comprising using the assembly of any one of embodiment 1 through 12 to remove the cannulated screw.

The method of embodiment 3, wherein said cannulated screw is from the biological tissue removed by: passing the second end of the screw tip engagement device through a cannula of a cannulated screw that is disposed in the biological tissue, wherein the cannulated screw has a screw head, a screw tip, and a screw longitudinal axis that extends from the screw head to the screw tip; after the hook of the screw tip engagement device has passed through the cannula of the cannulated screw and thereby reformed the hook, applying a force to the screw tip engagement device proximate the first end, wherein the force is applied in a direction along the screw longitudinal axis and away from the screw head; withdrawing the cannulated screw from the biological tissue.

The method of embodiment 3, further comprising engagement element a portion of the screw with the fourth end of the screw extractor.

The method of embodiment 18, wherein the portion of the screw comprises the screw head.

LIST OF EMBODIMENTS

In some embodiments the invention encompasses the following non-limiting list of embodiments:

1. A screw tip engagement device, comprising:
   an elongated body comprising a first end, a second end opposite the first end, and a screw tip contact member disposed proximate the second end;
   wherein the elongated body is formed of a resilient material;
   wherein the elongated body has a first longitudinal axis;
   wherein the elongated body further comprises a canted portion proximate the screw tip contact member, the canted portion being canted relative to the longitudinal axis.
2. The device of embodiment 1, wherein the screw tip contact member is configured to engage a tip of a cannulated bone screw.
3. The device of embodiment 1 or embodiment 2, wherein the body comprises spring steel with a low-alloy manganese, medium-carbon steel or high-carbon steel with a high yield strength, or a combination thereof.
4. The device of embodiment 1 or embodiment 2, wherein the body comprises a memory metal.
5. The device of embodiment 4, wherein the memory metal is nitinol.
6. An assembly, comprising:
   a proximal screw engagement element having a third end, a fourth end opposite the third end, and a first hollow channel extending from the third end to the fourth end;
   wherein the fourth end is configured to engage a portion of a cannulated bone screw;
   a screw tip engagement device comprising a first end, a second end and a screw tip contact member disposed proximate the second end;
   wherein the screw tip engagement device is disposed in the first hollow channel such that the first end of the screw tip engagement device extends outside the first end of the first hollow channel and the second end of the screw tip engagement device extends outside the fourth end of the first hollow channel; and
   optionally, a gripping element holding the screw tip engagement device proximate the first end of the screw tip engagement device.
7. The assembly of embodiment 6, wherein the proximal screw engagement element further comprises a first handle.
8. The assembly of embodiment 6 or embodiment 7, wherein the gripping element further comprises a second handle.
9. The assembly of any one of embodiments 6 through 8, wherein the gripping element further comprises a second hollow channel extending therethrough, wherein a portion of the screw tip engagement device proximate the first end extends into the second hollow channel.
10. The assembly of embodiment 8, wherein the portion of the screw tip engagement device proximate the first end extends through the second hollow channel.
11. The assembly of any one of embodiments 6 through 9, wherein the fourth end comprises a screwdriver assembly.
12. The assembly of any one of embodiments 6 through 10, wherein the screw tip engagement device and the proximal screw engagement element have exterior surfaces that are composed of biologically compatible material.
13. The assembly of embodiment 12, wherein the screw tip engagement device comprises a deformably resilient wire.
14. The assembly of embodiment 13, wherein the wire is composed of an elastic material selected from the group consisting of spring steel with a low-alloy manganese, medium-carbon steel or high-carbon steel with a high yield strength, or a combination thereof.
15. The assembly of any one of embodiments 6 through 13, wherein the proximal screw engagement element is rotatable about the wire independent of the gripping element.
16. The assembly of any one of embodiments 6 through 14, wherein the screw tip engagement device is adapted to pass through a cannula of a cannulated screw.
17. The assembly of any one of embodiments 6 through 15, wherein said screw tip contact member comprises a bend and a point.
18. A kit, comprising:
   a proximal screw engagement element having a first end, a fourth end opposite the first end, and a hollow channel extending from the first end to the fourth end;
      wherein the fourth end is configured to hold a portion of a cannulated bone screw;
   a screw tip engagement device comprising a first end, a second end and a screw tip contact member disposed proximate the second end; and
   a screw tip engagement device grasping element configured to hold the screw tip engagement device in a position relative to the proximal screw engagement element.
19. The kit of embodiment 18, wherein the proximal screw engagement element further comprises a first handle.
20. The kit of embodiment 18 or 19, wherein the screw tip engagement device grasping element further comprises a second handle.
21. The kit of any one of embodiments 18 through 19, wherein the screw tip engagement device grasping element further comprises a second hollow channel extending therethrough.
22. The kit of any one of embodiments 18 through 20, wherein the screw tip engagement device comprises a deformably resilient wire comprising a hook structure proximate the second end.
23. The kit of embodiment 21, wherein the hook structure can elastically bias toward the wire when the second end of the wire is passed through a hollow channel that is not deformed by the screw tip contact member passing through it.
24. A method for removing a cannulated screw from biological tissue, the method comprising using the device of any one of embodiments 1 through 5 or the assembly of any one of embodiments 6 through 17 to remove the cannulated screw.

25. The method of embodiment 24, wherein said cannulated screw is from the biological tissue removed by;
passing the second end of the screw tip engagement device through a cannula of a cannulated screw that is disposed in the biological tissue, wherein the cannulated screw has a screw head, a screw tip, and a screw longitudinal axis that extends from the screw head to the screw tip;
after the hook of the screw tip engagement device has passed through the cannula of the cannulated screw and thereby reformed the hook, applying a force to the screw tip engagement device proximate the first end, wherein the force is applied in a direction along the screw longitudinal axis and away from the screw head; and
withdrawing the cannulated screw from the biological tissue.
26. The method of embodiment 25, further comprising engagement element a portion of the screw with the fourth end of the screw extractor.
27. The method of embodiment 26, wherein the portion of the screw comprises the screw head.

3.0 EXAMPLES

The following examples are provided solely to illustrate the present invention and are not intended to limit the scope of the invention, described herein.

Example 1. Construction of a Screw Tip Engagement Device

A screw tip engagement device was constructed using a wire (50 cm long by 3 mm diameter) made of stainless steel 316L. The device depicted in FIG. 1 was produced from the wire by hand-filing the wire using a filer, Dremel clamps, and a jeweler saw.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

All publications mentioned herein are incorporated by reference to the extent they support the present invention.

We claim:

1. An assembly for engaging a cannulated bone screw with a screw tip and a screw head opposite the screw tip, comprising:
a screw tip engagement device comprising an elongated body having a first end, a second end opposite the first end, and a screw tip contact member disposed proximate the second end, the elongated body comprises a canted portion proximate the screw tip contact member;
a proximal screw engagement element having a third end, a fourth end opposite the third end, and a first hollow channel extending from the third end to the fourth end; and
a gripping element holding the screw tip engagement device proximate the first end of the screw tip engagement device;
wherein the screw tip engagement device comprises a deformably resilient wire that is configured to deform the screw tip contact member into a compressed state while traveling through the first hollow channel of a proximal screw engagement element and to return to an uncompressed state when the screw tip contact member engages a portion of the screw tip of the cannulated bone screw;
wherein the fourth end of the proximal screw engagement element is configured to engage a portion of the screw head of the cannulated bone screw;
wherein the screw tip contact member of the screw tip engagement device is configured to engage a portion of the screw tip of the cannulated bone screw outside of a cannula of the cannulated bone screw;
wherein the screw tip engagement device is movable to pass through the first hollow channel such that the first end of the screw tip engagement device extends outside the third end of the first hollow channel and such that the second end of the screw tip engagement device travels past and extends outside the fourth end of the first hollow channel; and
wherein the proximal screw engagement element is rotatable about the deformably resilient wire independent of the gripping element.

2. The assembly of claim 1, wherein the proximal screw engagement element further comprises a first handle that is rotatable relative to the screw tip engagement device.

3. The assembly of claim 1, wherein the gripping element further comprises a second hollow channel extending therethrough, wherein a portion of the screw tip engagement device proximate the first end extends into the second hollow channel.

4. The assembly of claim 3, wherein the portion of the screw tip engagement device proximate the first end extends through the second hollow channel.

5. The assembly of claim 1, wherein the fourth end comprises a screwdriver assembly.

6. The assembly of claim 1, wherein the screw tip engagement device and the proximal screw engagement element have exterior surfaces that are composed of biologically compatible material.

7. The assembly of claim 1, wherein the deformably resilient wire is composed of an elastic material selected from the group consisting of spring steel with a low-alloy manganese, medium-carbon steel or high-carbon steel with a high yield strength, or a combination thereof.

8. The assembly of claim 1, wherein the screw tip engagement device is adapted to pass through the cannula of the cannulated bone screw.

9. The assembly of claim 1, wherein said screw tip contact member comprises a bend and a point.

10. The assembly of claim 1,
wherein the elongated body of the screw tip engagement device extending from the first end to the second end has a first longitudinal axis; and
wherein the canted portion extends along a second longitudinal axis that is canted relative to the first longitudinal axis when the deformably resilient wire is in a decompressed state, the first longitudinal axis being non-parallel with the second longitudinal axis.

11. A kit for removing a cannulated bone screw, comprising:
a screw tip engagement device including an elongated body with a first end, a second end opposite the first end, and a screw tip contact member disposed proximate the second end;

a proximal screw engagement element having a third end, a fourth end opposite the third end, and a first hollow channel extending from the third end to the fourth end; and a screw tip engagement device grasping element configured to hold the screw tip engagement device in a position relative to the proximal screw engagement element, wherein the screw tip engagement device comprises a deformably resilient wire that is configured to deform the screw tip contact member into a compressed state while traveling through a first hollow channel of a proximal screw engagement element and to return to an uncompressed state when the screw tip contact member engages a portion of a screw tip of the cannulated bone screw;

wherein the fourth end of the proximal screw engagement element is configured to engage a portion of a screw head of the cannulated bone screw;

wherein the screw tip engagement device is movable to pass through the first hollow channel such that the first end of the screw tip engagement device extends outside the third end of the first hollow channel, and such that the second end of the screw tip engagement device travels past and extends outside the fourth end of the first hollow channel;

wherein the screw tip contact member is configured to engage a screw tip of the cannulated bone screw outside of the cannula of the cannulated bone screw; and wherein the proximal screw engagement element is rotatable about the deformably resilient wire independent of the screw tip engagement device grasping element.

12. The kit of claim 11, wherein the proximal screw engagement element further comprises a first handle that is rotatable relative to the screw tip engagement device.

13. The kit of claim 11, wherein the screw tip engagement device grasping element further comprises a second handle.

* * * * *